(12) United States Patent
Yamauchi

(10) Patent No.: US 8,075,753 B2
(45) Date of Patent: Dec. 13, 2011

(54) GAS SENSOR

(75) Inventor: Masanobu Yamauchi, Kariya (JP)

(73) Assignee: Denso Corporation, Kariya (JP)

( * ) Notice: Subject to any disclaimer, the term of this patent is extended or adjusted under 35 U.S.C. 154(b) by 689 days.

(21) Appl. No.: 12/254,334

(22) Filed: Oct. 20, 2008

(65) Prior Publication Data

US 2009/0101504 A1 Apr. 23, 2009

(30) Foreign Application Priority Data

Oct. 18, 2007 (JP) ................................. 2007-271584
Jul. 30, 2008 (JP) ................................. 2008-195723

(51) Int. Cl.
*G01N 27/407* (2006.01)
(52) U.S. Cl. ....... 204/428; 204/424; 439/637; 73/23.31; 219/202
(58) Field of Classification Search .................. 204/424, 204/428; 219/202–209; 73/23.31, 23.32; 439/33, 260, 637, 913
See application file for complete search history.

(56) References Cited

U.S. PATENT DOCUMENTS

| 4,824,550 | A  | * | 4/1989 | Ker et al. ...................... 204/427 |
| 2003/0101569 | A1 | * | 6/2003 | Watanabe et al. ............ 29/592.1 |
| 2005/0145013 | A1 | * | 7/2005 | Hayashi et al. .............. 73/31.05 |
| 2007/0157939 | A1 | * | 7/2007 | Nakagawa ................... 131/346 |

FOREIGN PATENT DOCUMENTS

| JP | U-559-006768 | 1/1984 |
| JP | A-H04-310856 | 11/1992 |
| JP | A-2002-082090 | 3/2002 |
| JP | A-2002-156353 | 5/2002 |
| JP | 2005-310767 | 11/2005 |
| JP | A-2008-139218 | 6/2008 |
| JP | A-2008-298731 | 12/2008 |

* cited by examiner

Primary Examiner — Kaj K Olsen
Assistant Examiner — Susan Thai
(74) Attorney, Agent, or Firm — Nixon & Vanderhye PC

(57) ABSTRACT

The gas sensor includes a sensor element, a heater for heating the sensor element, the heater having a roughly cylindrical shape, a housing into which the sensor element is inserted to be held therein, and a terminal unit disposed so as to cover a rear end portion of the heater on a rear end side of the housing. The terminal unit includes a pair of insulators, a pair of metal terminals each of which is located inside a corresponding one of the pair of the insulators and in contact with a corresponding one of a pair of electrode pads provided on a surface of the rear end portion of the heater, and a pressing member pressing the pair of the insulators in a direction that the pair of the insulators approach each other. The pair of the insulators are located out of contact with each other. The rear end portion of the heater is contact-supported at at least three contact points by the terminal unit.

10 Claims, 10 Drawing Sheets

GAS SENSOR

CROSS-REFERENCE TO RELATED APPLICATION

This application is related to Japanese Patent Applications No. 2007-271584 filed on Oct. 18, 2007, and No. 2008-195723 filed on Jul. 30, 2008, the contents of which are hereby incorporated by reference.

BACKGROUND OF THE INVENTION

1. Field of the Invention

The present invention relates to a gas sensor fox detecting a concentration of a specific gas component in a gas under measurement.

2. Description of Related Art

Generally, an exhaust system of an internal combustion engine of a vehicle is provided with a gas sensor for detecting a concentration of a specific gas component such as oxygen or nitrogen oxide contained in an exhaust gas. It is known that a sensor element of such a gas sensor is inserted into a housing to be held therein as shown, for example, in Japanese Patent Application Laid-open No. 2005-310767. As shown in FIG. 18, the gas sensor described in this Patent Document includes a heater 93 of a roughly cylindrical shape inserted inside the sensor element of the gas sensor to heat the sensor element. On the rear end side of the housing, an insulator is disposed so as to cover the rear end portion 930 of the heater 93.

As shown in FIG. 18, in this gas sensor, a pair of electrode pads 933 provided in the rear end portion 930 of the heater 93 are crimp-fixed inwardly by a crimp member 911 in such a state that the pair of the electrode pads 933 are in electrical contact with a pair of contact terminals 952 connected to an external power supply.

In the above gas sensor, the heater 93 is contact-supported in a state that the pair of the electrode pads are held between the pair of the contact terminals 952. That is, each of the pair of the contact terminals 952 contacts corresponding one of the pair of the electrode pads only at a single point. Accordingly, the heater 93 is not in the state of being firmly held by the pair of the contact terminals 952 at the rear end portion 930 thereof. Hence, there is a possibility that the heater 93 vibrates around the contact points between the pair of the electrode pads 933 and the pair of the contact terminals 952. In this case, the electrode pads 933 may be worn at the contact points.

SUMMARY OF THE INVENTION

The present invention provides a gas sensor comprising:
a sensor element for detecting a concentration of a specific gas component in a gas under measurement;
a heater for heating the sensor element, the heater having a roughly cylindrical shape;
a housing into which the sensor element is inserted to be held therein; and
a terminal unit disposed so as to cover a rear end portion of the heater on a rear end side of the housing;
wherein the terminal unit includes a pair of insulators, a pair of metal terminals each of which is located inside a corresponding one of the pair of the insulators and in contact with a corresponding one of a pair of electrode pads provided on a surface of the rear end portion of the heater, and a pressing member pressing the pair of the insulators in a direction that the pair of the insulators approach each other, the pair of the insulators being located out of contact with each other,
the rear end portion of the heater being contact-supported at at least three contact points by the terminal unit.

According to the present invention, it is possible to provide a gas sensor whose electrode pads can be prevented from wearing.

Other advantages and features of the invention will become apparent from the following description including the drawings and claims.

BRIEF DESCRIPTION OF THE DRAWINGS

In the accompanying drawings:
FIG. 3 is a diagram showing a contact point between the rear end portion of a heater and the terminal unit in the gas sensor of the first embodiment.

PREFERRED EMBODIMENTS OF THE INVENTION

In the following description, the term "front end side" means a side of a gas sensor from which the gas sensor is inserted into an exhaust pipe of an internal combustion engine, for example, and the term "rear end side" means the opposite side of the gas sensor. Also, in the following description, the term "contact-supported" includes not only "supported by point contact", but also "supported by line contact", and "supported by surface contact".

First Embodiment

Figure 1:
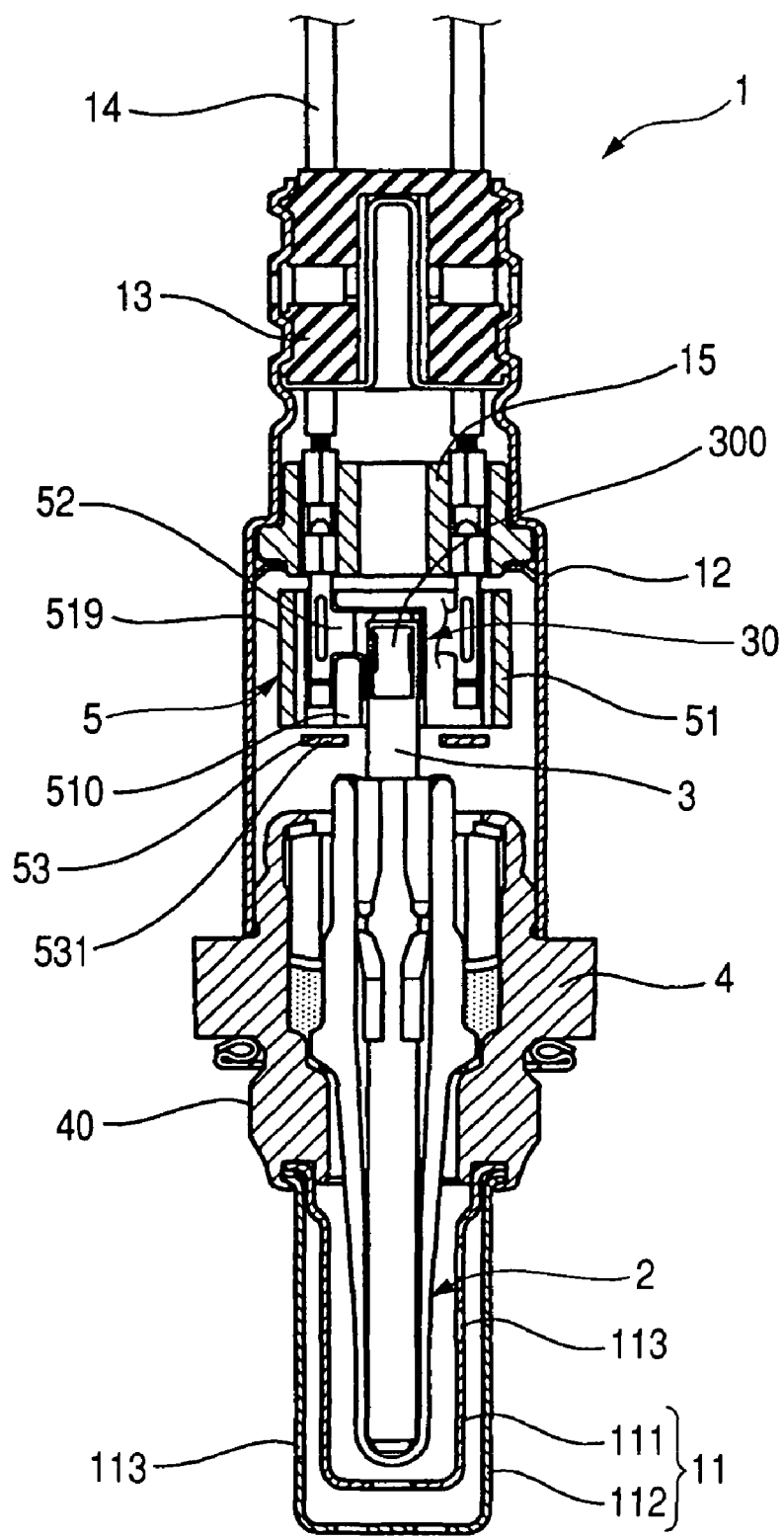
FIG. 1 is a longitudinal cross-sectional view of a gas sensor of a first embodiment of the invention.

FIG. 1 is a longitudinal cross-sectional view of a gas sensor 1 according to a first embodiment of the invention. As shown in FIG. 1, the gas sensor 1 includes a sensor element 2 for detecting a concentration of a specific gas component in a gas under measurement, a heater 3 which is for heating the sensor element 2 and has a roughly cylindrical shape, a housing 4 into which the sensor element 2 is inserted to be held therein, and a terminal unit 5 disposed at the rear end side of the housing 4 so as to cover a rear end portion 30 of the heater 3.

As shown in FIGS. 1 to 7, the terminal unit 5 includes a pair of insulators 51, a pair of metal terminals 52 each of which is disposed on an inner surface 510 of a corresponding one of the insulators 51 and in contact with a corresponding one of a pair of electrode pads 300 provided on a surface of the rear end portion 30 of the heater 3, and a pressing member 53 pressing the pair of the insulators 51 in the direction that they approach each other.

As shown in FIGS. 3 and 5 to 7, the pair of the insulators 51 are located out of contact with each other. The rear end portion 30 of the heater 3 is contact-supported by the terminal unit 5 at three or more points. As described later, in this embodiment, the rear end portion 30 of the heater 3 is contact-supported by the terminal unit 5 at six points.

As explained above, the gas sensor 1 includes the sensor element 2, the heater 3, the housing 4, and the terminal unit 5. The housing 4, which is made of metal, is screwed to an exhaust pipe of an internal combustion engine of a vehicle at a thread portion 40 thereof formed on its front end side.

As shown in FIG. 1, the housing 4 is provided with an element cover 11 including an inner cover 111 for covering a front end portion of the sensor element 2 and an outer cover 112 located surrounding the inner cover 111. Each of the inner cover 111 and the outer cover 112 is formed with a gas introducing hole 113. The housing 4 is joined with an atmosphere side cover 12 covering the terminal unit 5 at its rear end side. The rear end portion of the atmosphere side cover 12 is closed by a rubber bush 13 through which external lead wires 14 pass. The sensor element 2 is a cup-type sensor element of a bottomed cylinder shape. The heater 3 is a roughly cylindrically shaped heater inserted inside the sensor element 2.

Next, the components constituting the terminal unit 5 are explained. As described in the foregoing, the terminal unit 5 is constituted by the pair of the insulators 51, the pair of the metal terminals 52, and the two pressing members 53.

Figure 3:
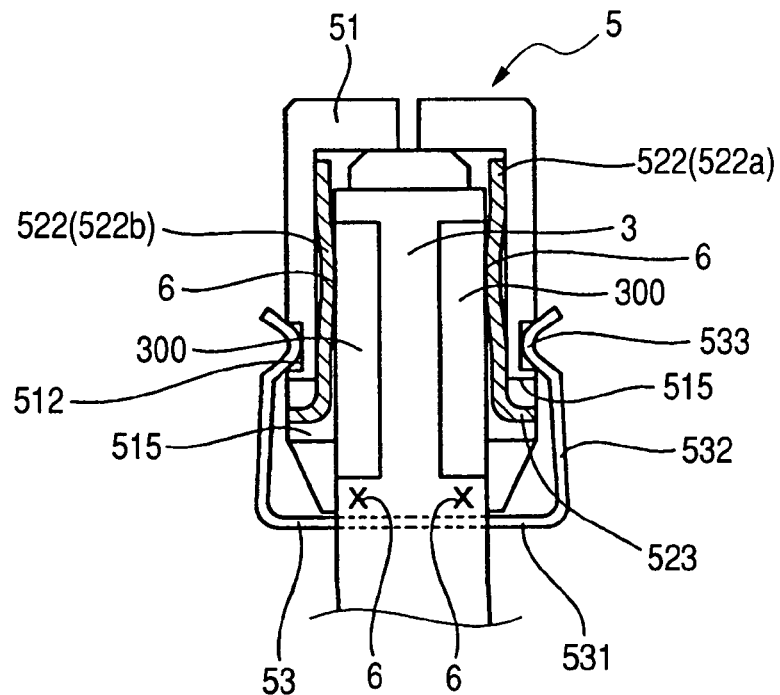
FIG. 3 is an A-A cross section of FIG. 2.
Figure 4:
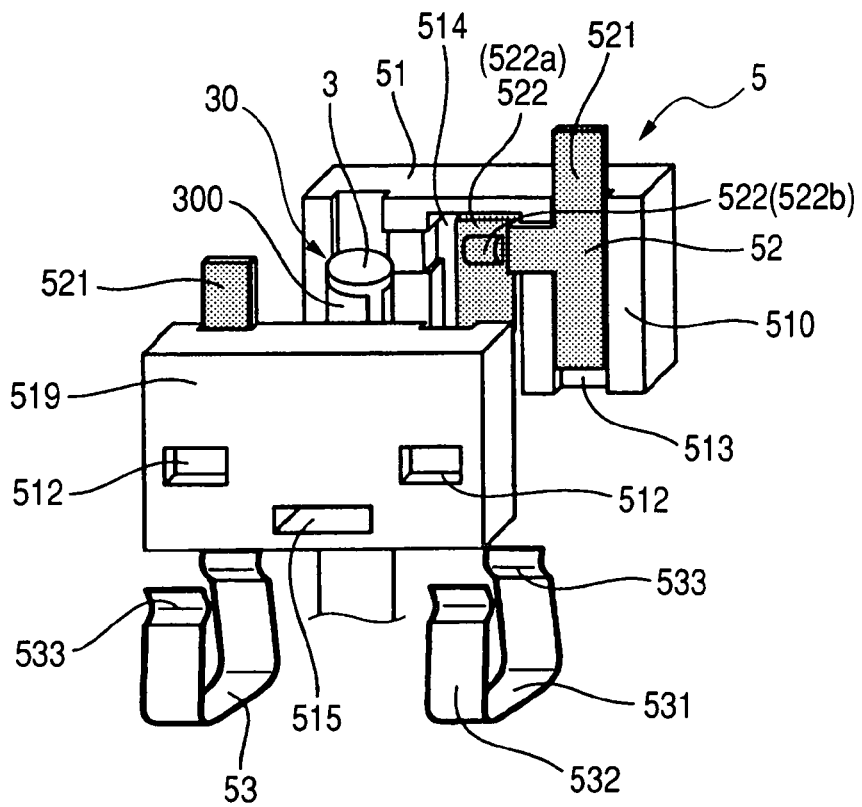
FIG. 4 is a perspective view of the terminal unit included in the gas sensor of the first embodiment.

The pressing member 53, which is formed of a plate-like spring member having a C-shape as shown in FIGS. 3 and 4, includes a flat plate-like bottom plate portion 531, and a pair of rising portions 532 provided at both ends of the bottom plate portion 531 and bent so as to extend from the same surface of the bottom plate portion 531. Each of the rising portions 532 is formed with an abutment portion 533 which abuts on the insulator 51 at near its front end portion.

Figure 6:
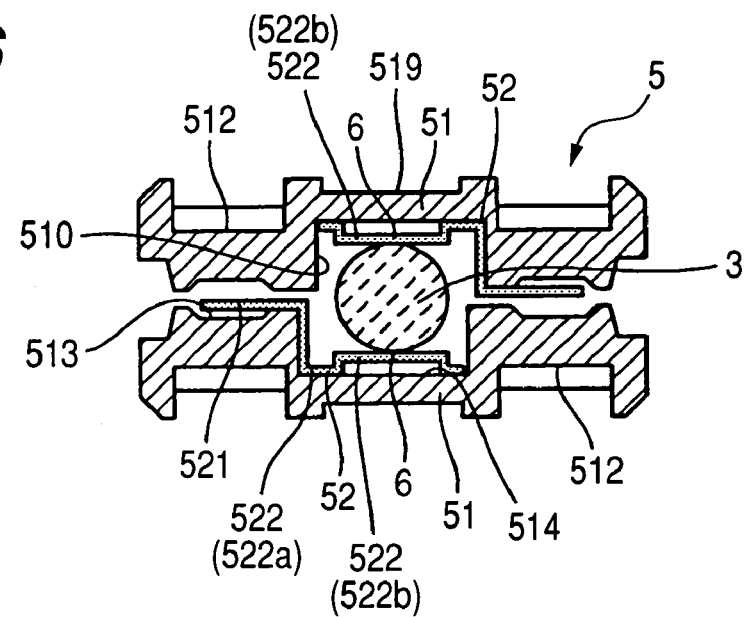
FIG. 6 is a B-B cross section of FIG. 2.

The metal terminal 52 includes a lead portion 521 connected to the external lead wire 14, and a contact terminal portion 522 in contact with the electrode pad 300. As shown in FIG. 6, the lead portion 521 and the contact terminal portion 522 are formed such that their cross-sections perpendicular to the longitudinal direction of the gas sensor are parallel to each other and shifted stepwise from each other. In this embodiment, the contact terminal portion 522 itself of the metal terminal 52 does not generate a biasing force to move radially inwardly.

As shown in FIG. 6, the contact terminal portion 522 includes a base plate portion 522a having a plate like shape in the cross section in the longitudinal direction in which a contact point at which the rear end portion 30 of the heater 3 is contact-supported is included, and a contact portion 522b projecting radially inwardly in this cross section at the rear end portion 30 of the heater 3. The contact portion 522b is formed to arc in the longitudinal direction.

As shown in FIGS. 2, 4, 6, 8 and 9, the rear end portion 30 of the heater 3 and the terminal unit 5 are in single-point contact with each other at each of the contact terminal portions 522 formed in the pair of the metal terminals 52, and at each of the pair of the electrode pads 300. Accordingly, the electrode pad 300 is electrically connected to an external power supply (not shown) through the external lead wire 14 and the metal terminal 52.

Figure 5:
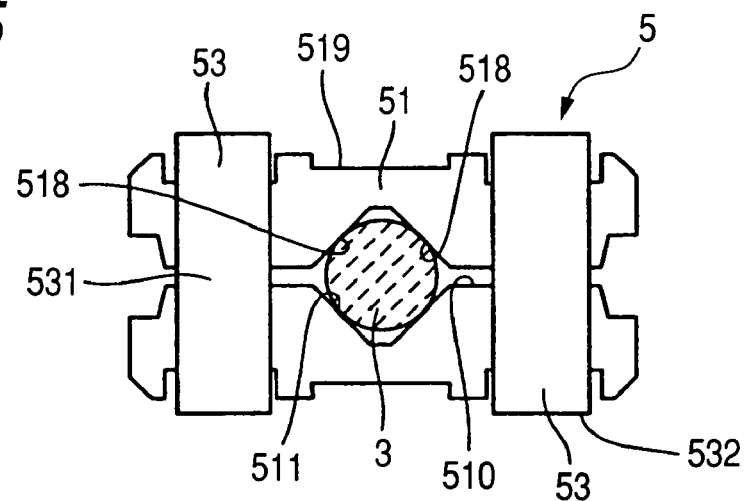
FIG. 5 is a bottom view of the terminal unit included in the gas sensor of the first embodiment.
Figure 7:
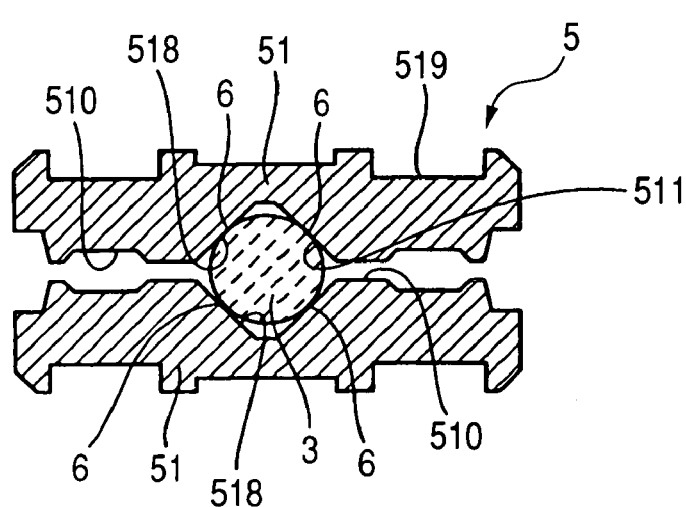
FIG. 7 is a C-C cross section of FIG. 2.

As shown in FIGS. 5 and 7, the insulator 51 includes heater abutment portions 511 whose cross-section in the direction perpendicular to the longitudinal direction has a roughly V-shape. The heater abutment portion 511 may be a pair of abutment surfaces 518 which form an angle of 80-100 degrees therebetween. In this embodiment, the heater abutment portion 511 is formed of a pair of abutment surfaces 518 which form an angle of 90 degrees therebetween.

As shown in FIGS. 3 and 4, the insulator 51 is formed with a hole portion 515 penetrating the inner surface 510 and an outer surface 519 of the insulator 51, and housing the contact terminal portion 522 in a state of a front end portion 523 of the contact terminal portion 522 being bent outwardly. As shown in FIGS. 2, 4, 6 and 7, the inner surface 510 of the insulator 51 is formed with a lead positioning portion 513 for positioning the lead portion 521, and a terminal positioning portion 514 for positioning the contact terminal portion 522. As show in FIGS. 3 and 4, the outer surface 519 of the insulator 51 is formed with a concave seat portion 512 in which the abutment portion 533 of the pressing member 53 is seated.

The structure of the terminal unit 5 is as follows. As shown in FIG. 4, each of the pair of the insulators 51 is provided with the metal terminal 52. The lead portion 521 of the metal terminal 52 is fitted into the lead positioning portion 513, and the contact terminal portion 522 of the metal terminal 52 is fitted into the terminal positioning portion 514. As shown in FIGS. 5 to 7, the pair of the insulators 51 are located such that they hold therebetween the rear end portion 30 of the heater 3, and their inner surface 510 on which the metal terminals are disposed are opposed to each other in a state of being out of contact with each other.

As shown in FIGS. 3 and 4, the two pressing members 53 hold therebetween the pair of the insulators 51 from the front end side of the insulators 51 in such a state that the abutment portions 533 of the pressing members 53 are seated respectively in the corresponding concave seat portions 512 formed in the outer surface 519 of the insulator S1.

Next, the contact state between the rear end portion 30 of the heater 3 and the terminal unit 5 is explained with reference to FIGS. 2, 3, and 6 to 9. The reference numeral 6 in FIG. 6 denotes the contact point between the rear end portion 30 of the heater 3 and the terminal unit 5.

Figure 8:
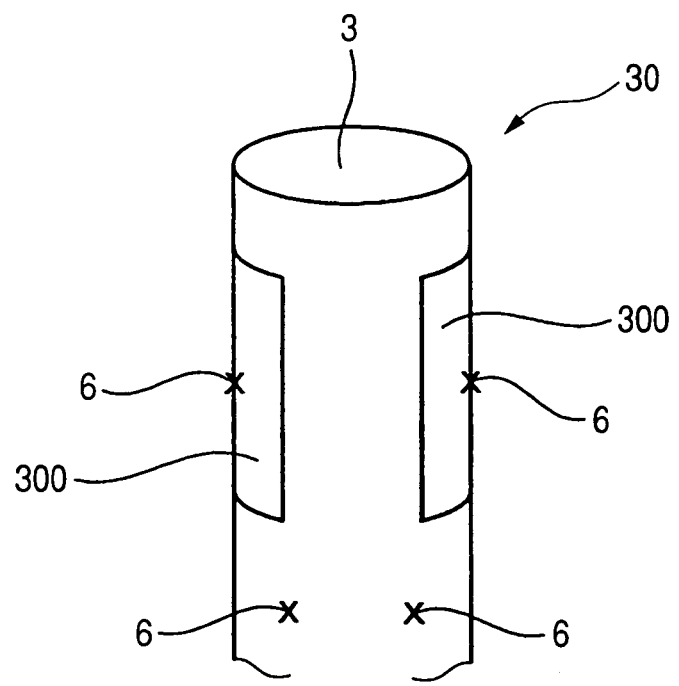
Figure 9:
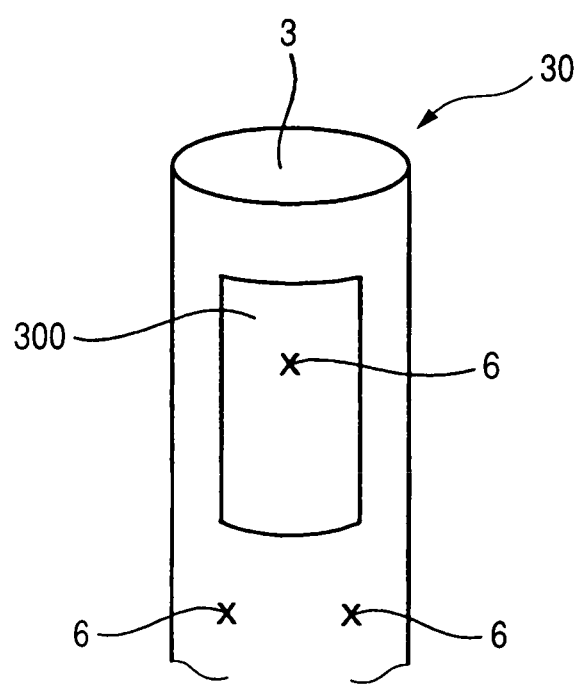
FIG. 9 is a perspective view of the heater included in the gas sensor of the first embodiment.
Figure 10:
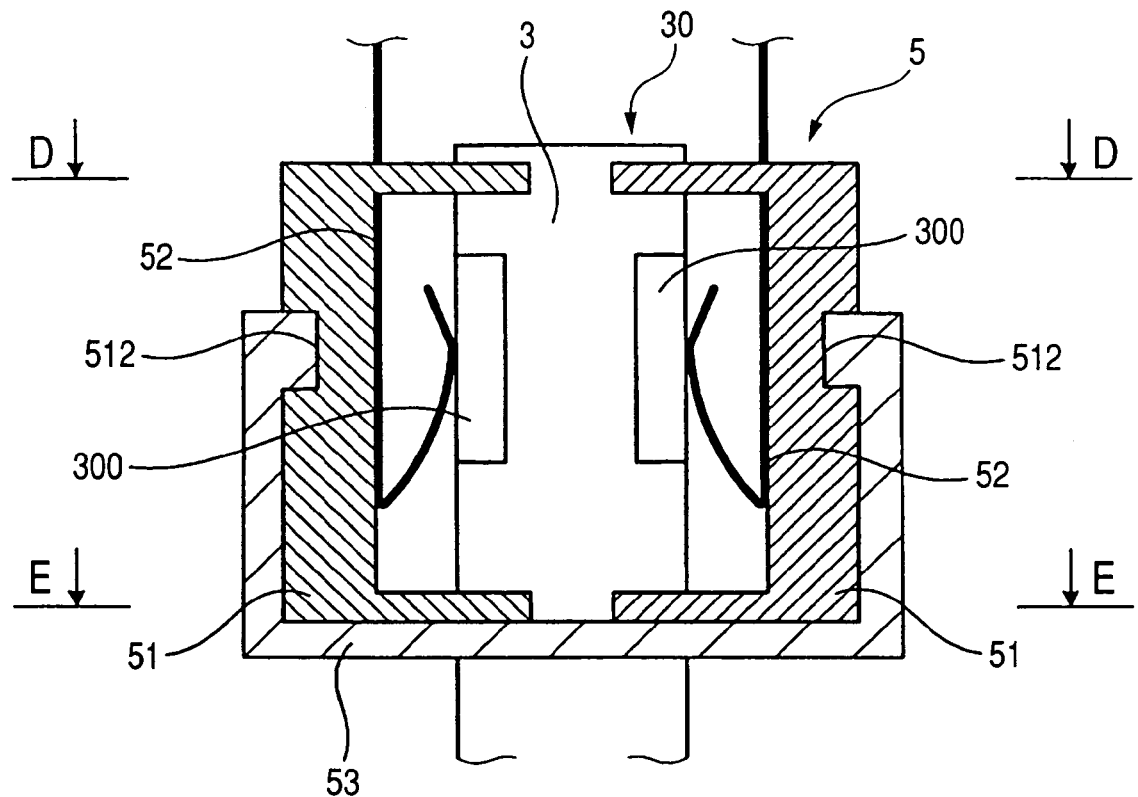
FIG. 10 is a longitudinal cross-sectional view of a terminal unit included in a gas sensor of a second embodiment of the invention.

As shown in FIGS. 2, 3, 6, 8 and 9, each of the contact terminal portions 522 and a corresponding one of the electrode pads 300 are in single-point contact with each other. Accordingly, the pair of the contact terminal portions 522 and the pair of the electrode pads 300 are in two-point contact with each other. Also, as shown in FIGS. 7 to 9, the rear end portion 30 of the heater 3 and the heater abutment portion 511 are in two-point contact with each other. Accordingly, the heater 3 is contact-supported at four points by the heater abutment portions 511 of the pair of the insulators 51 on its front end side beyond the electrode pads.

As explained above, the pair of the electrode pads 300 of the heater 3 are in two-point contact with the pair of the metal terminals 52, and the rear end portion 30 of the heater 3 is in four-point contact with the heater abutment portions 511. In short, the rear end portion 30 of the heater 3 is contact-held at six points in total by the terminal unit 5.

Next, mounting procedure of the rear end portion 30 of the heater 3 and the terminal unit 5 is explained. First, the metal terminal 52 is put on the inner surface 510 of the insulator 51 such that the lead portion 521 of the metal terminal 52 is fitted to the lead positioning portion 513, and the contact terminal portion 522 of the metal terminal 52 is fitted to the terminal positioning portion 514. Thereafter, the pressing members 53 are mounted so as to hold the insulator 51 therebetween to complete assembling of the terminal unit 5. At this time, as shown in FIG. 3, the pressing member 53 presses the pair of the insulators 51 in the direction that they approach each other between the longitudinal position of the contact points at which the pair of the metal terminals 52 support the rear end portion 30 of the heater 3, and the longitudinal position of the contact points at which the pair of the insulators 51 support the rear end portion 30 of the heater 3.

Next, the pair of the insulators 51 in the terminal unit 2 are pulled away from each other until a clearance larger than a diameter of the rear end portion 30 of the heater 3 is provided between the pair of the metal terminals 52 by applying a force greater than the pressing force of the pressing member 53.

Subsequently, the rear end portion 30 of the heater 3 is inserted between the pair of the metal terminals 52. At this time, as shown in FIG. 3, the front end portion 52 of the contact terminal portion 522 of the metal terminal 52 is housed in the hole portion 515. Accordingly, since the rear end portion 30 of the heater 3 does not hit the front end portion 523 of the metal terminal 52, the heater 3 can be prevented from being damaged when the rear end portion 30 of the heater 3 is inserted between the pair of the metal terminals 52.

Although the pressing member 53 is a plate-like spring in this embodiment, the pressing member 53 may have any shape if it has the function of pressing the pair of the insulators 51 in the direction that they approach each other.

Next, the operation and action of this embodiment are described. The rear end portion 30 of the heater 3 is contact-supported at three or more contact points by the terminal unit 5. In more detail, the rear end portion 30 of the heater 3 is in contact with each of the pair of the metal terminals 52 at at least one point, and further in contact with the terminal unit 5 at at least one point. According to this embodiment, since the rear end portion 30 of the heater 3 is contact-supported at three or more contact points, it is possible to prevent the heater 3 from swinging like a pendulum. Accordingly, it becomes possible to suppress the rear end portion 30 of the heater 3 and the terminal unit 5 from swaying with respect to each other.

This makes it possible for the electrode pad 300 and the metal terminal 52 to move together, to thereby prevent the heater 3 from swinging around the contact portion between the electrode pad 300 and the metal terminal 52. As a result, the electrode pad 300 can be prevented from wearing at the contact portion with the metal terminal 52 when the gas sensor 1 is applied with vibration from the outside. The pair of the insulators 51 are mounted out of contact with each other. Accordingly, it is possible to transmit the pressing force of the pressing member 53 to the contact point 6 between the rear end portion 30 of the heater 3 and the terminal unit 5, to thereby ensure a force enough to hold the rear end portion 30 of the heater 3 with respect to the terminal unit 5.

The rear end portion 30 of the heater 3 is contact-supported at six or more points by the terminal unit B. Accordingly, it is possible to sufficiently suppress the rear end portion 30 of the heater 3 and the terminal unit 5 from swaying with respect to each other. The insulator 51 includes the heater abutment portions 511 whose cross-section in the direction perpendicular to the longitudinal direction has a roughly V-shape. Accordingly, since the rear end portion 30 of the heater 3 is contact-supported at four points by the heater abutment portions 511 in the pair of the insulators 51, it is possible to prevent the rear end portion 30 of the heater 3 and the terminal unit 5 from swaying with respect to each other more effectively.

The pressing member 53 presses the pair of the insulators 51 in the direction that they approach each other between the longitudinal position of the contact points at which the pair of the metal terminals 52 support the rear end portion 30 of the heater 3, and the longitudinal position of the contact points at which the pair of the insulators 51 support the rear end portion 30 of the heater 3. This makes it possible to reliably apply the pressing force to the pair of the metal terminals 52 and the pair of the insulators 51.

Each of the metal terminals 52 includes the contact portion 522b projecting radially inwardly in the cross section in the longitudinal direction in which the contact point at which the rear end portion 30 of the heater 3 is contact-supported is included. Accordingly, it is possible to improve reliability of the contact between the electrode pad 300 and the metal terminal 52, and to stabilize the contact load.

As explained above, according to the first embodiment, a gas sensor having high resistance to wear of the electrode pads can be provided.

In this embodiment, to hold the heater 3 in the position shown in FIG. 9, the rear end portion 30 of the heater 3 is contact-supported at a single point by the metal terminal 52, and contact-supported at two points by the insulator S1. However, the method of holding the heater 3 is not limited to the one described in the first embodiment. For example, to hold the heater 3 in the position shown in FIG. 9, the rear end portion 30 of the heater 3 may be contact-supported at three points by the metal terminal 52. Alternatively, the rear end portion 30 of the heater 3 may be contact-supported at two points by the metal terminal 52, and further contact-supported at a single point by the insulator 51.

Second Embodiment

Figure 11:
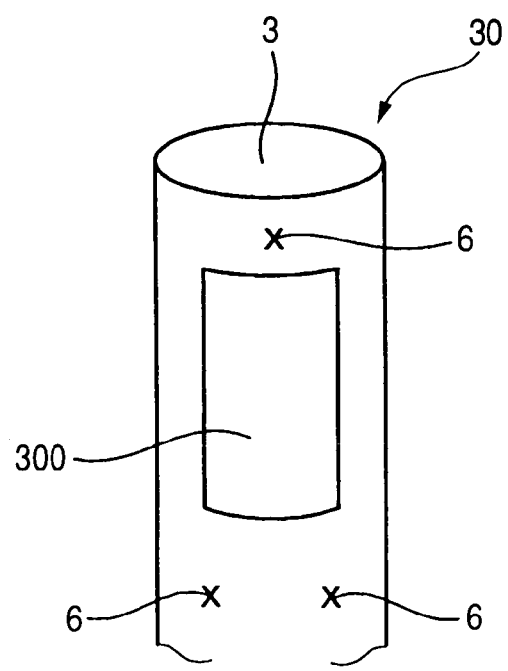
FIG. 11 is a diagram showing a contact point between the rear end portion of a heater and the terminal unit in the gas sensor of the second embodiment.
Figure 12:
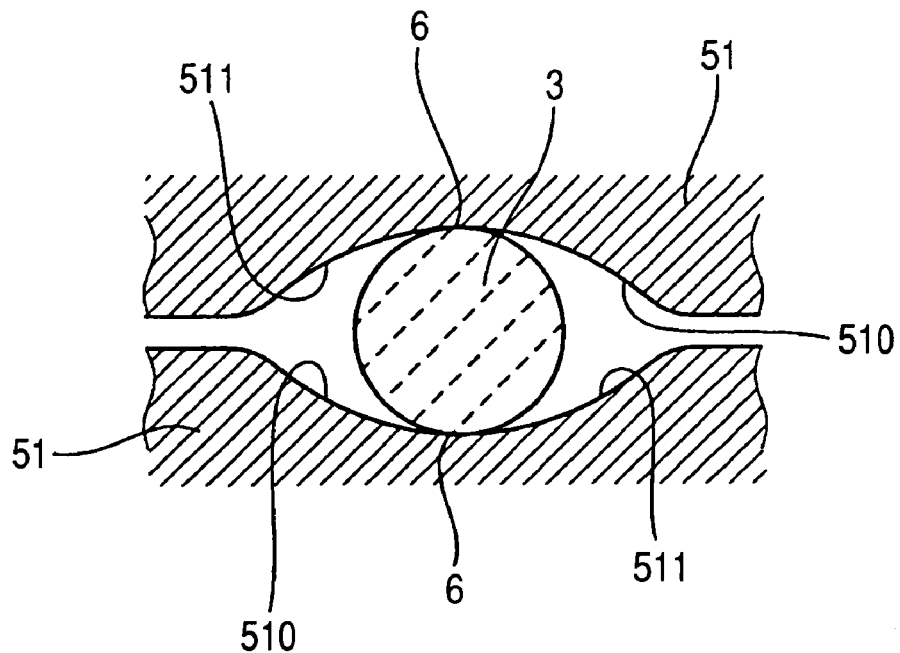
FIG. 12 is a D-D cross section of FIG. 10.
Figure 13:
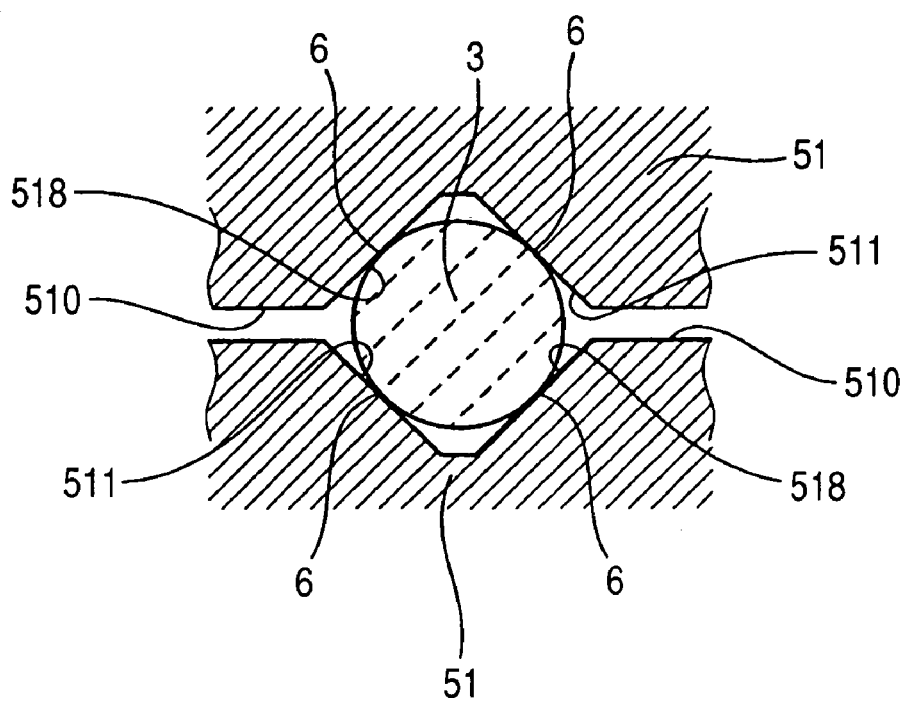
FIG. 13 is an E-E cross section of FIG. 10.

The second embodiment of the invention describes a gas sensor in which the terminal unit 5 is so configured that the metal terminal 52 is biased radially inwardly. In FIGS. 11 to 13, the reference numeral 6 denotes the contact point between the rear end portion 30 of the heater 3 and the terminal unit 5.

As shown in FIG. 11, the rear end portion 30 of the heater 3 is contact-supported at two or more points whose longitudinal positions differ from each other by each of the pair of the insulators 51. In this embodiment, the rear end portion 30 of the heater 3 is contact-supported at six points on the rear and front end sides the pair of the electrode pads 300 by the pair of the insulators 51.

In more detail, as shown in FIG. 12, the rear end portion 30 of the heater 3 is in single-point contact with the front end side of the insulator 51 at the heater abutment portion 511 formed to have a curved surface shape at the rear end side of the insulator 51. Accordingly, as shown in FIGS. 11 and 12, the rear end portion 30 of the heater 3 is in two-point contact with the rear end side of the pair of the insulators 51.

As shown in FIG. 13, the insulator 51 includes at its front end side the heater abutment portions 511 whose cross-section in the direction perpendicular to the longitudinal direction has a roughly V-shape. The rear end portion 30 of the heater 3 is in two-point contact with the insulator 51 at each of the heater abutment portions 511. Accordingly, as shown in FIGS. 11 and 12, the rear end portion 30 of the heater 3 is in contact with the front end side of the pair of the insulators 51 at four points. Hence, in this embodiment, the rear end portion 30 of the heater 3 is in contact with the terminal unit 5 at six points in total.

It should be noted that although the metal terminal 52 is biased radially inwardly, the metal terminal 52 is in contact with the electrode pad 300 only for making electrical connection between the electrode pad 300 and the external power supply, and not for contact-supporting the rear end portion 30 of the heater 3. In this embodiment, the heater abutment portion 511 having a curved surface shape is formed on the rear end side of the inner surface 510 of the insulator 51. However, instead, the heater abutment portion 511 having a roughly V-shape in the cross-section in the direction perpendicular to the longitudinal direction may be formed on the rear end side of the inner surface 510 of the insulator 51, in addition to on the front end side. In this case, the rear end portion 30 of the heater 3 and the terminal unit 5 are in contact with each other at eight contact points. As for the other components, the second embodiment is the same as the first embodiment.

According to the second embodiment, since the metal terminal 52 is biased radially inwardly, the reliability of contact between the electrode pad 300 and the metal terminal 52 can be improved. The rear end portion 30 of the heater 3 is contact-supported at two or more points whose longitudinal positions differ from each other by each of the pair of the insulators 51. This makes it possible to contact-support the rear end portion 30 of the heater 3 more reliably, and prevent wear of the electrode pad 300 more effectively.

Particularly, according to this embodiment, since the rear end portion 30 of the heater 3 is contact-supported on the rear and front end sides of the electrode pad 300 by the insulator 51, the heater 3 can be stably held by the insulator 51. This makes it possible to prevent the rear end portion 30 of the heater 3 and the terminal unit 5 from swaying with respect to each other more effectively. As for the other components, the second embodiment is the same as the first embodiment.

Third Embodiment

Figure 2:
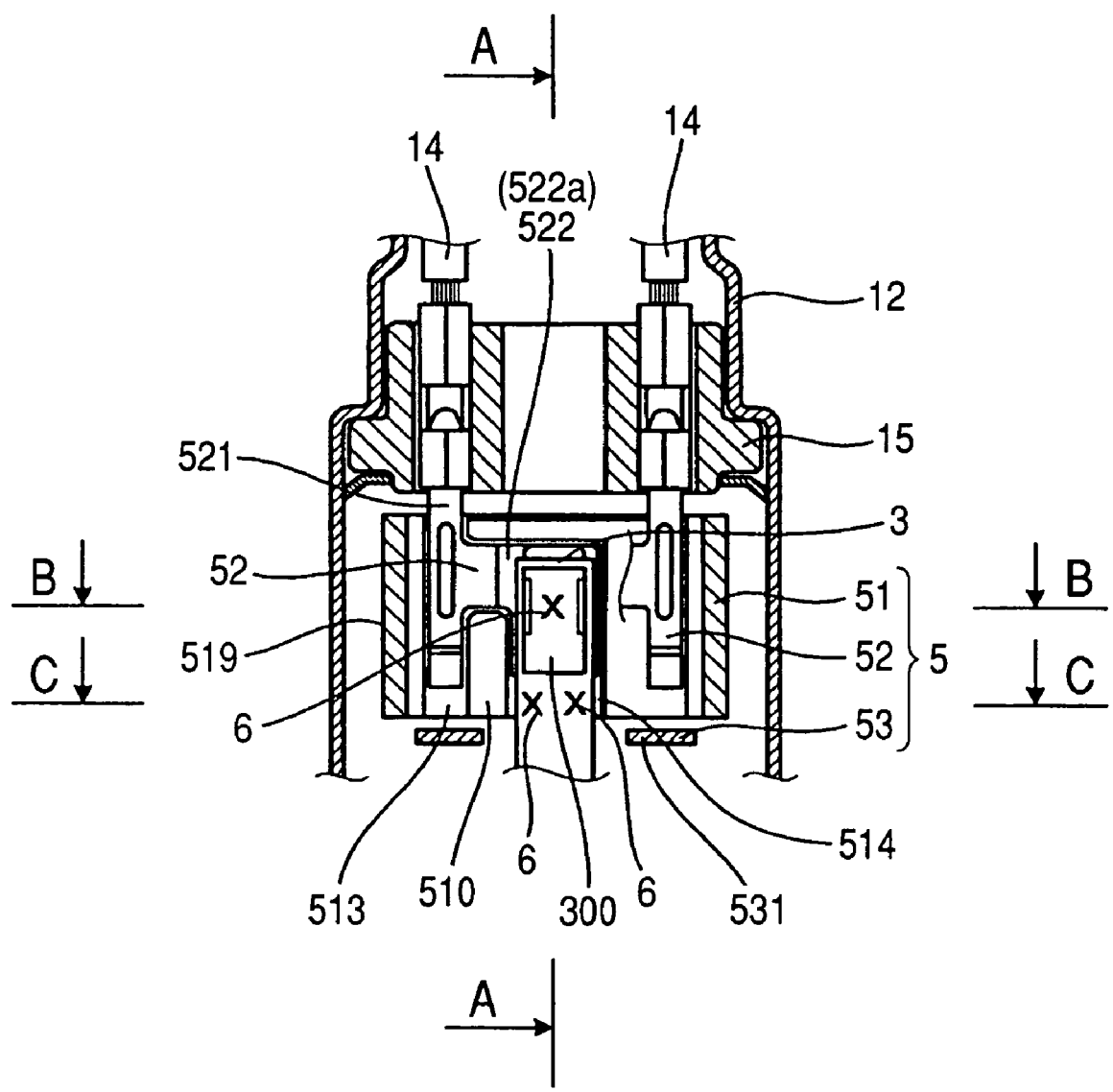
FIG. 2 is a longitudinal cross-sectional view of a terminal unit included in the gas sensor of the first embodiment.
Figure 14:
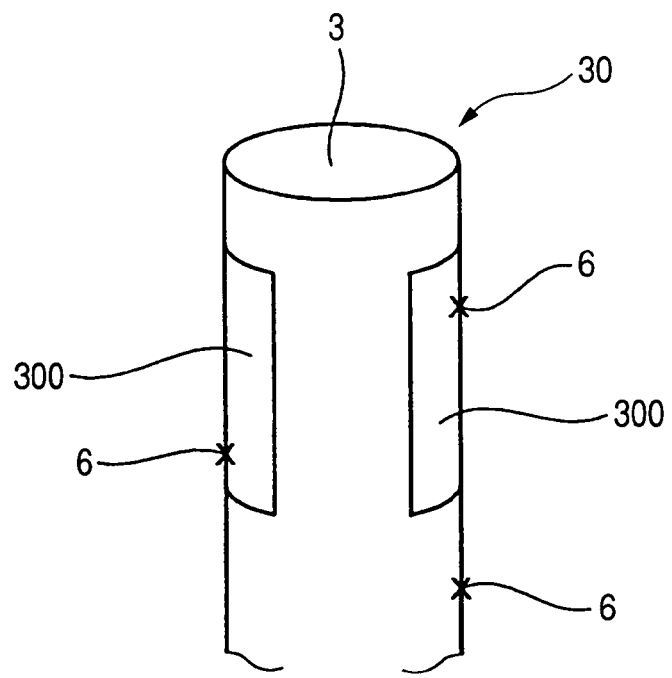
FIG. 14 is a diagram showing a contact point between the rear end portion of a heater and a terminal unit in a gas sensor of a third embodiment of the invention.
Figure 15:
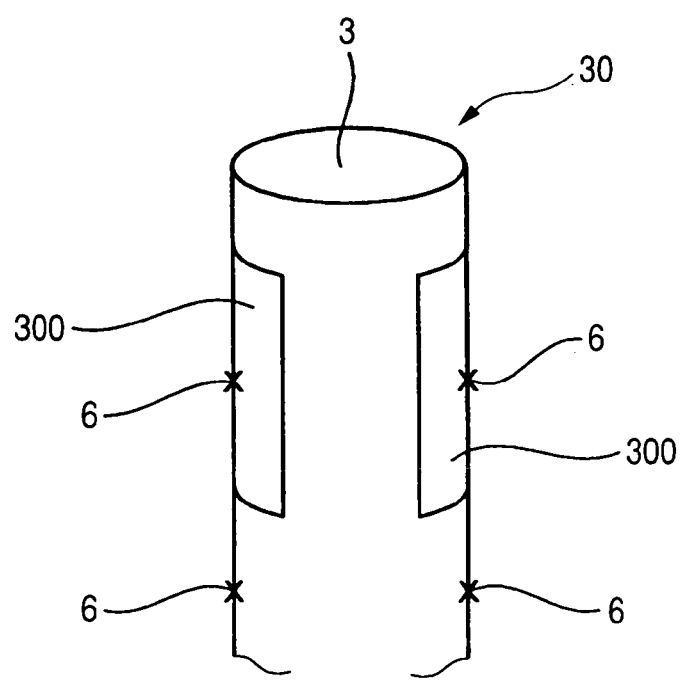
FIG. 15 is a diagram showing another contact point between the ear end portion of the heater and the terminal unit in the gas sensor of the third embodiment of the invention.

A gas sensor according to a third embodiment of the invention differs from the gas sensors according to the above embodiments in the state of contact between the rear end portion 30 of the heater 3 and the terminal unit 5. In FIG. 14 showing the contact state between the rear end portion 30 of the heater 3 and the terminal unit 5 in this embodiment, and FIG. 15 showing the contact state between the rear end portion 30 of the heater 3 and the terminal unit 5 in a modification of this embodiment, the reference numeral 6 denotes the contact point between the rear end portion 30 of the heater 3 and the terminal unit 5. In FIGS. 14 and 15, the reference numerals identical to those in FIG. 2 represent the same or corresponding components.

In this embodiment, as shown in FIG. 14, each of the contact terminal portions 522 of the pair of the metal terminals 52 are in contact with each of the pair of the electrode pads 300 at a single point in such a state that the longitudinal positions of the two contact points of the pair differ from each other. The heater 3 is in single-point contact with the inner surface 510 of the insulator 51 on its front end side beyond the electrode pad 300. Accordingly, in this embodiment, the rear end portion 30 of the heater 3 and the terminal unit 5 are in contact with each other at three points.

In the modification of the third embodiment shown in FIG. 15, each of the contact terminal portions 522 of the pair of the metal terminals 52 is in contact with each of the pair of the electrode pads 300 at a single point in such a state that the longitudinal positions of the two contact points of the pair are the same with each other. The rear end portion 30 of the heater 3 and the inner surface 510 of the insulator 51 are in contact with each other also on a line longitudinally extending toward the front end side from the contact point 6 and between the electrode pad 300 and the contact terminal 522. Accordingly, in the modification of the third embodiment, the heater 3 and the terminal unit 5 are in contact with each other at four points in total.

As for the other components, the third embodiment and the modification of the third embodiment are the same as the first embodiment.

Fourth Embodiment

Figure 16:
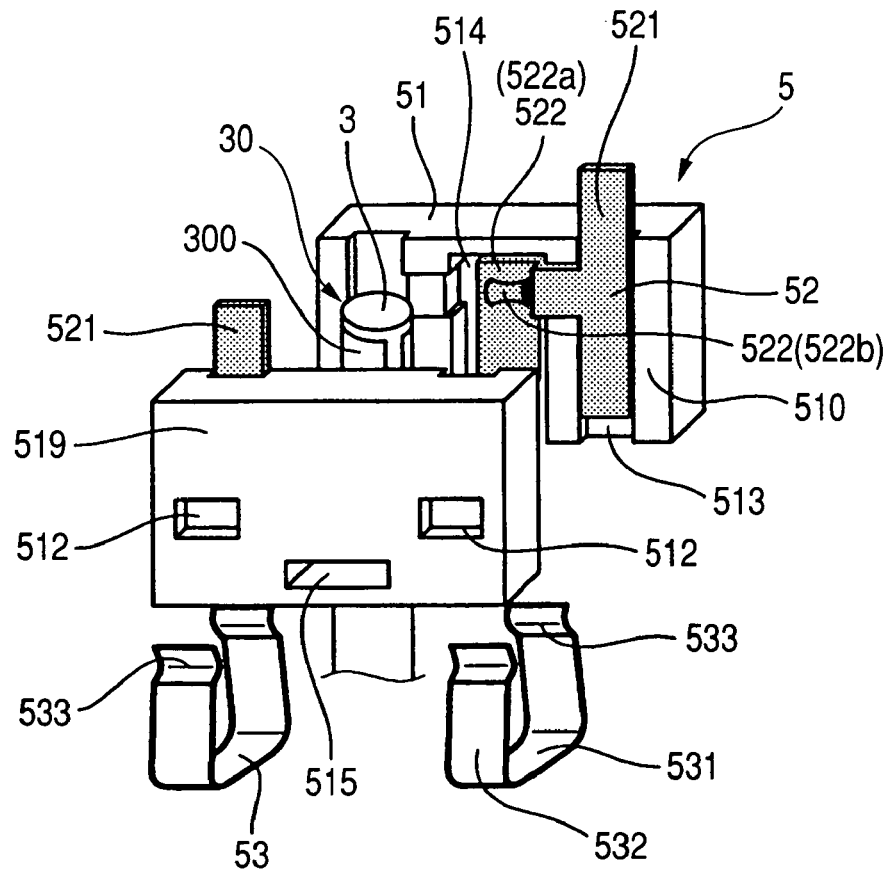
FIG. 16 is a perspective view of a terminal unit included in a gas sensor of a fourth embodiment of the invention.
Figure 17:
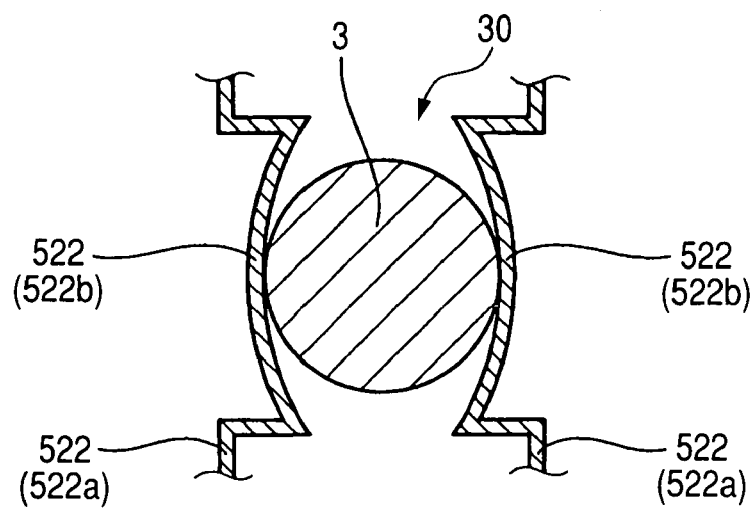
FIG. 17 is a diagram showing a state of contact between a rear end portion of a heater and a pair of metal terminals in the gas sensor of the fourth embodiment.
Figure 18:
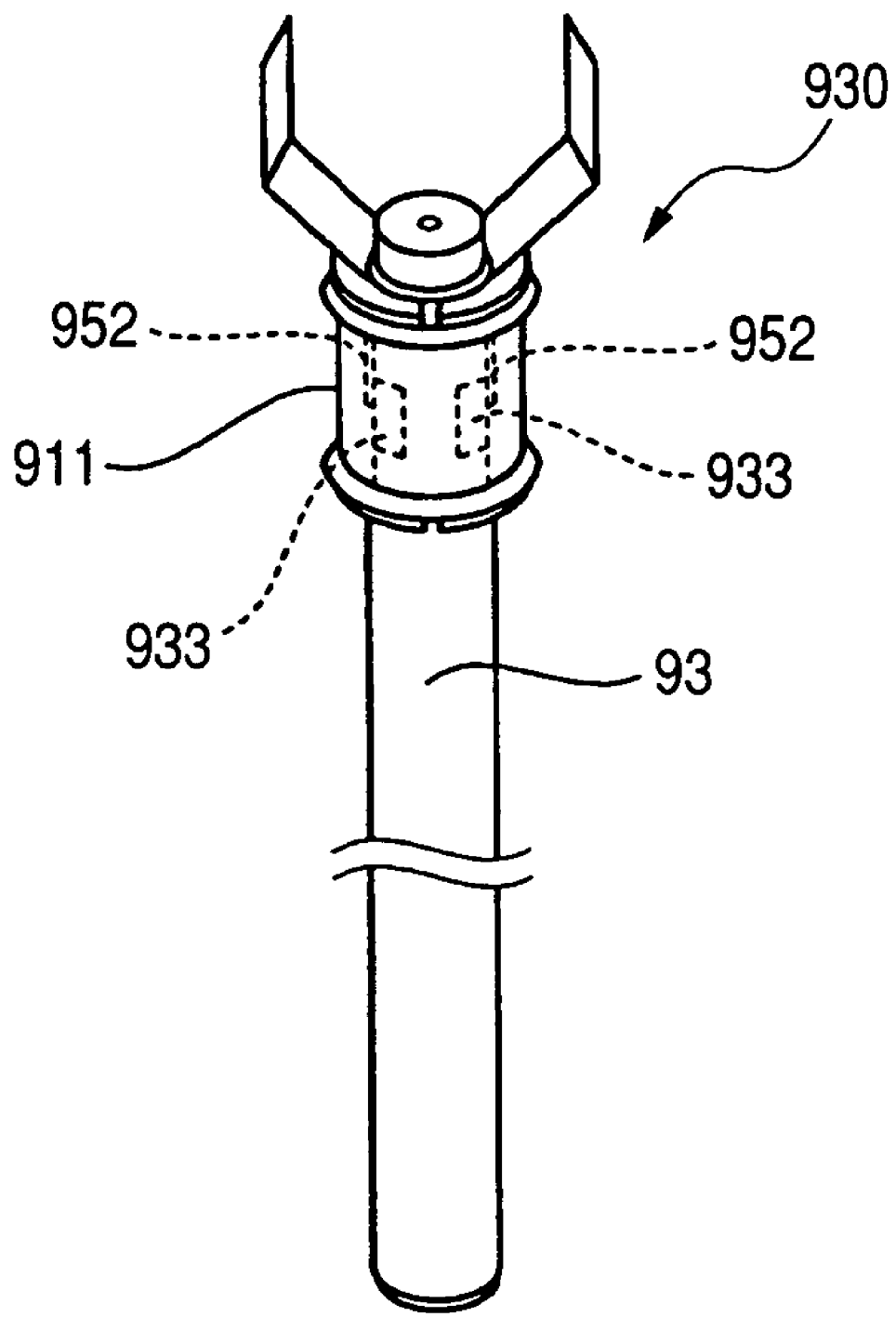
FIG. 18 is a perspective view of a heater included in a conventional gas sensor.

FIG. 16 is a perspective view of the terminal unit 5 of a gas sensor 1 according to a fourth embodiment of the invention. FIG. 17 is a lateral cross-sectional view of the heater 3 and the contact terminal portion 522 of the terminal unit 5 of the gas sensor 1 according to the fourth embodiment of the invention. As shown in FIGS. 16 and 17, the gas sensor 1 of this embodiment includes the contact portion 522b projecting radially outwardly of the rear end portion 30 of the heater 3 in the cross section perpendicular to the longitudinal direction in which the contact point at which the rear end portion 30 of the heater 3 is contact-supported is included. In more detail, the contact terminal portion 522 includes the base plate portion 552a having a plate like shape, and the contact portion 522b located more radially inwardly of the rear end portion 30 of the heater 3 than the base plate portion 552a, and formed to have a curved surface projecting radially outwardly. In this embodiment, the contact portion 522b and the electrode pad 300 are in contact with each other. As for the other components, the fourth embodiment is the same as the first embodiment.

The fourth embodiment provides, in addition to the advantages provided by the first embodiment, the advantages that the rear end portion 30 of the heater 3 and the terminal unit 5 can be sufficiently suppressed from swaying with respect to each other, and the rear end portion 30 of the heater 3 is firmly held by the terminal unit 5 to thereby prevent the rear end portion 30 of the heater 3 from vibrating laterally.

The present invention can be applied to a gas sensor mounted on an exhaust pipe of an internal combustion engine of a vehicle, such as an a limit-current type A/F sensor for measuring an air-fuel ratio of an exhaust gas of the internal combustion engine, an oxygen sensor for measuring an oxygen concentration of the exhaust gas, or NOx sensor for detecting deterioration of a ternary catalyst mounted on the exhaust pipe.

The above explained preferred embodiments are exemplary of the invention of the present application which is described solely by the claims appended below. It should be understood that modifications of the preferred embodiments may be made as would occur to one of skill in the art.

What is claimed is:

1. A gas sensor comprising:
   a sensor element for detecting a concentration of a specific gas component in a gas under measurement;
   a heater for heating the sensor element, the heater having a roughly cylindrical shape;
   a housing into which the sensor element is inserted to be held therein; and
   a terminal unit disposed so as to cover a proximal end portion of the heater on a proximal end side of the housing, wherein the terminal unit includes a pair of insulators, a pair of metal terminals disposed on internal surfaces of the insulators and being in contact with a pair of electrode pads provided on a surface of the proximal end portion of the heater, and a pressing member pressing the pair of the insulators in a direction that the pair of the insulators approach each other, the pair of the insulators being in contact with the heater and out of contact with each other, the proximal end portion of the heater being contact-supported at three or more support points by the terminal unit.

2. The gas sensor according to claim 1, wherein the proximal end portion of the heater is contact-supported at two support points by the pair of the metal terminals, and contact-supported at two or more support points by the pair of the insulators.

3. The gas sensor according to claim 2, wherein the support points of the proximal end portion of the heater by the pair of the metal terminals and the support points of the proximal end portion of the heater by the pair of the insulators differ from each other in a longitudinal position, and the pressing member presses the pair of the insulators in a direction that the pair of the insulators approach each other between a longitudinal position of the support points of the proximal end portion of the heater by the pair of the metal terminals and a longitudinal position of the support points of the proximal end portion of the heater by the pair of the insulators.

4. The gas sensor according to claim 1, wherein the pair of the metal terminals include a contact portion projecting radially inwardly of the proximal end portion of the heater in a cross section in a longitudinal direction including the support points at which the proximal end portion of the heater is contact-supported by the pair of the metal terminals.

5. The gas sensor according to claim 1, wherein the pair of the metal terminals include a contact portion projecting radially outwardly of the proximal end portion of the heater in a cross section in a direction perpendicular to a longitudinal direction including the support points at which the proximal end portion of the heater is contact-supported by the metal terminals.

6. The gas sensor according to claim 1, wherein the proximal end portion of the heater is contact-supported at six or more support points by the terminal unit.

7. The gas sensor according to claim 1, wherein the insulators include a heater abutment portion whose cross section in a direction perpendicular to a longitudinal direction has a roughly V-shape, the insulators being in abutment with the proximal end portion of the heater at the heater abutment portion.

8. The gas sensor according to claim 1, wherein the metal terminals are biased radially inwardly.

9. The gas sensor according to claim 1, wherein the proximal end portion of the heater is contact-supported at two or more points different in longitudinal position by the insulators.

10. The gas sensor according to claim 9, wherein the proximal end portion of the heater is contact-supported on sides of proximal and distal ends of the electrode pads by the insulators.

* * * * *